| United States Patent [19] | [11] | 4,390,528 |
|---|---|---|
| Najjar | [45] | Jun. 28, 1983 |

[54] TUFTSINYL-TUFTSIN

[75] Inventor: Victor A. Najjar, Cohasset, Mass.

[73] Assignee: Research Corporation, New York, N.Y.

[21] Appl. No.: 321,786

[22] Filed: Nov. 16, 1981

[51] Int. Cl.$^3$ ..................... A61K 37/02; C07C 103/52
[52] U.S. Cl. ............................. 424/177; 260/112.5 R
[58] Field of Search .................. 260/112.5 R; 424/177

[56] References Cited

U.S. PATENT DOCUMENTS 4,353,823  10/1982  Chippens et al. ............ 424/112.5 R

OTHER PUBLICATIONS

Chemical Abstracts, vol. 86, 1977, p. 155942, Abstract No. 155947p.
Chemical Abstracts, vol. 85, 1976, p. 87591, Abstract No. 87594y.

*Primary Examiner*—Delbert R. Phillips
*Assistant Examiner*—F. T. Moezie
*Attorney, Agent, or Firm*—Scully, Scott, Murphy and Presser

[57] ABSTRACT

The compound L-threonyl-L-lysyl-L-prolyl-L-arginyl-L-threonyl-L-lysyl-L-prolyl-L-arginine, its pharmacologically acceptable salts and derivatives, and certain of its optical isomers are useful for stimulating or inhibiting phagocytosis or pincytosis in mammals.

12 Claims, No Drawings

TUFTSINYL-TUFTSIN

The invention described herein was made under a grant or award from the National Institutes of Health.

BACKGROUND OF THE INVENTION

This invention relates to novel, therapeutically useful polypeptides which exhibit varying degrees of phagocytosis or pinocytosis stimulation in mammals, including humans. It relates also to pharmaceutical compositions containing such polypeptides as well as to their use in mammalian patients in need of such stimulation or inhibition.

The gamma globulin fraction of whole mammalian blood is the fraction which contains the antibodies utilized by the body in resisting invasion by antigens. More specifically, the gamma globulin fraction of mammalian blood is the fraction containing substances which the body utilizes in combatting attack by infectious diseases. The production of antibodies is a natural defense mechanism of the body stimulated by the presence of antigens in the body. Normally specific antibodies are produced to combat specific antigens and, in many instances, the body thereafter maintains an antibody level against the specific antigen or infectious organism so that reinfection is inhibited and often prevented.

The use of the gamma globulin fraction of whole mammalian blood as a therapeutic agent has therefore attracted considerable medical attention since it would seem possible to utilize this fraction from an individual who has successfully overcome an infection to stimulate resistance to that same infection in another individual.

Unfortunately, this approach to prophylaxis has not proved sufficiently fruitful and cannot be used on a long term basis except in cases of a gamma globulinemia. There are many reasons for this. One is that patients often reject gamma globulin, especially on repeated dosages because they treat the gamma globulin as an antigen and develop antibodies to reject it. Another is that an increase above the normal gamma globulin level in the blood may have untoward effects such as seen in hypergamma-globulinemia. Moreover, even in those instances where gamma globulin treatment can be employed, the treatment is not as effective as desired because the bulk of it tends to stay in the blood of the patients rather than diffuse into the tissues which is situs of infection.

It has been known for some time that a tetrapeptide L-threonyl-L-lysyl-L-propyl-L-arginine (tuftsin) has the ability to stimulate phagocytosis and subsequent destruction of bacteria by blood polymorphonuclear leucocytes especially neutrophilic leucocytes in mammals. It also stimulates pinocytosis to the same extent allowing the cells to obtain nourishment from the surrounding medium.

It has been discovered that tuftsin when administered to a patient initially degrades to a tripeptide lysyl-prolyl-arginine, and that this tripeptide acts as an inhibitor to the therapeutic action of tuftsin. Thus, if large amounts of tuftsin are administered, for example, parenterally a rather complex series of reactions takes place. One is the desired therapeutically useful reaction, another is the formation of the inhibitory tripeptide and the third is the inhibitory reaction. The rate of the last two reactions is, unfortunately, so high that the administration of higher doses of the therapeutic agent is counterproductive. As more is administered, more of the inhibitory tripeptide is produced and less of the tuftsin is available to fulfill its therapeutic purpose.

THE INVENTION

It has now been discovered that the problem aforesaid can be alleviated by administration of the dimer of tuftsin, tuftsinyl-tuftsin, or more precisely L-threonyl-L-lysyl-L-prolyl-L-arginyl-L-threonyl-L-lysyl-L-prolyl-L-arginine. This compound upon administration to a mammal metabolizes to produce tuftsin at a slow steady rate and at a low but therapeutically effective level. The amount of tuftsin produced subsequent to the administration of a therapeutically effective amount of tuftsinyl-tuftsin is high enough so that a therapeutically useful effect is achieved, but not so high that the concentration of the inhibitory tripeptide becomes a problem.

For convenience in describing this invention, the conventional abbreviations used by skilled peptide chemists for the various amino acids and certain useful reagents will be employed. They are all familiar to those skilled in the art, but for clarity they are listed below.

Lys—Lysine
Thr—Threonine
Pro—Proline
Arg—Arginine
Z—Carbobenzoxy
OBzl—Benzyl
Tos—Tosyl
TFA—Trifluoroacetic acid
Boc—Tertiary butyloxycarbonyl
DCC—Dicyclohexylcarbodiimide
TFMS—Trifluoromethanesulfonic acid Tuftsinyl-tuftsin is L-Thr-L-Lys-L-Pro-L-Arg-L-Thr-L-Lys-L-Pro-L-Arginine in which all of the amino acids are in the L-form. It is a stimulator of phagocytosis and pinocytosis.

It is, however, possible to regulate the degree of stimulation or, in fact, to completely reverse the stimulatory action and produce an inhibitor by producing derivatives of tuftsinyl-tuftsin or by preparing optical isomers of tuftsinyl-tuftsin.

This is most important because there are medical syndromes in which the patient is substantially incapable of phagocytosis or pinocytosis, as in the case of the splenectomized individual, and conditions where the phatgocytes are so active that other apparently normal cells are ingested. This occurs with patients afflicted with the so called collagen diseases such as rheumatoid arthritis and lupus erythematosus. Abnormal phagocytic activity in these patients may well be the cause of the destructive vascular lesions in the joints and various organs. Treatment with the inhibitory compounds of this invention is indicated in these patients.

It is also possible to produce compounds within the scope of this invention in which the tuftsin is released over a long period of time. These are sustained release agents.

The presently preferred inhibitory agents are optical isomers of tuftsinyl-tuftsin in which both Arg and Thr components are in the D-form. For long lasting activity, the terminal Thr and Arg will be in the D-form.

Tuftsinyl-tuftsin manifests antineoplastic activity against a variety of tumor cells including L1210 mouse leukemia cells, 316 mouse melanoma cells and Cloudman S-91 mouse melanoma cells.

In one experiment, 25 DBA/2 mice were injected each with 20 μg of the octapeptide intraperitoneally on days -7, -4 and 0. On the last mentioned day, L1210 cells were also injected intraperitoneally in experimental animals and solvent buffer alone in 25 control mice. The animals were observed daily and deaths recorded. The control animals were all dead by day 18, whereas the treated mice survived 32 days.

The products of this invention are useful mammalian therapeutic agents and are effective as stimulating or inhibiting agents at extremely low levels. The physician or veterinarian will determine the dosage which will be most suitable for a particular application. It may vary from patient to patient depending on the size of the patient, the condition under treatment and other factors which are readily evaluated by those skilled in the art. In any event, it will be an amount which is effective to induce the desired stimulatory or inhibitory effect in a patient in need of such treatment. It may vary with the method of administration, e.g. parenteral or oral.

The products of this invention may be administered alone but will generally be administered with pharmaceutically acceptable, non-toxic carriers, the proportions of which are determined by the suitability and chemical nature of the particular carrier, the chosen route of administration, and standard pharmaceutical practice. For example, in combatting various infections or in maintaining therapeutically effective levels in the blood or tissues, the selected agent or agents may be administered orally in the form of tablets or capsules containing such excipients as starch, milk sugar, certain types of clay, etc. They may be enteric so as to be more resistant to the acid with digestive enzymes of the stomach. For intravenous and intramuscular administration, they may be used in the form of a sterile solution containing other solutes, for example, enough saline or glucose to make the solution isotonic.

It is a particular advantage of the products of this invention that unlike many peptide bond containing therapeutic products, they can be administered orally because they are resistant to enzymatic hydrolysis by the enzymes of the lower digestive tract. Because of their amphoteric nature, they may be adsorbed for oral administration on non-toxic ion exchange resins which may be either anionic or cationic to achieve slow release either in the stomach or the intestines or both. Furthermore, adsorption on these resins makes them all the more resistant to enzyme destruction.

Another advantage arising from the amphoteric nature of the products of this invention is that they can be utilized in the form of pharmacologically acceptable salts which may be either metallic salts or acid addition salts. These salts have the advantage of water solubility and are particularly useful for parenteral administration. The metallic salts, especially the alkali metal salts are relatively stable and for that reason are preferred over acid addition salts. The sodium salts are especially preferred because of their ease of preparation.

The acids which may be used to prepare the pharmacologically acceptable acid addition salts of this invention are those containing nontoxic anions and include, for example, hydrochloric, sulfuric, phosphoric, acetic, lactic, citric, tartaric, oxalic, succinic, maleic, gluconic, saccharic, and the like acids.

These salts can be prepared by standard procedures well known to those skilled in the art, for example, by titration in aqueous media followed by freeze drying.

The products of this invention can be synthesized by any of a wide variety of techniques now available for the synthesis of simple and complex polypeptides. In general, these techniques involve stepwise synthesis by successive additions of amino acids to produce progressively larger molecules. The amino acids are linked together by condensation between the carboxyl group of one amino acid and the amino group of another amino acid to form a peptide bonds. In order to control these reactions, it is necessary to block the amino group of the one acid and the carboxyl group of the other. Necessarily, the blocking groups must be easily removed. The whole series of reactions must take place without causing racemization of the products. Certain amino acids have additional functional groups, for example, the hydroxyl group of threonine. It is usually necessary to block these additional groups with an easily removed blocking agent to that it does not interfere with the condensation reaction.

A large number of procedures have been devised by the art for the synthesis of polypeptides and a wide variety of blocking agents have been utilized. Most of these procedures are applicable to the synthesis of the class of polypeptides to which this invention pertains. No useful purpose would be served by describing the application of all of them. The presently preferred procedure is illustrated in the examples.

Any of a wide variety of non-toxic derivatives of the polypeptides of this invention can be usefully employed. The pharmacologically acceptable salts have been mentioned above. Amides, esters, acylated derivatives and others can be utilized.

For example, the compounds can readily be obtained as amides by reacting with thionyl chloride to form the acid chloride, and then with ammonia under conditions that minimize racemization to form the amide.

Enzymes are available in the body which will hydrolyze both amide and ester groups to regenerate the stimulatory activity of the acid. Both ester and amide derivatives are useful therapeutic agents because of their increased chemical stability compared with the free acids. They have altered rates of absorption or diffusion into the tissues and delayed excretion through the kidneys. They may be used in the form of pharmacologically acceptable salts.

Other useful derivatives may be obtained by modifying the free functional groups on the polypeptide backbone, for example, free hydroxyl groups or free amino groups. One very convenient class of derivatives is the class in which a free hydroxyl group of threonine is esterified with an alkanoyl or alkenoyl group containing up to eighteen or more atoms. Alternatively, an amino group, for example, the amino group of threonine or lysine can be acylated with an alkanoyl or alkenoyl group containing up to about eighteen carbon atoms. In both instances, the preferred derivatives are those in which the derivatizing groups contain from eleven to eighteen carbon atoms because the longer hydrocarbon chains impart increased lipid solubility to the molecules and enhance their transport across cell barriers.

Both types of derivatives may be prepared directly from the octapeptide, but are preferably prepared by incorporation in the peptide during synthesis of an amino acid with the selected group, for example, the alkanoyl group already in place.

The compounds of this invention can be used alone, but they will often be administered together with one or more other therapeutically active materials such as an antibiotic, antifungal or antiviral agent. One reason for this is to combat acute, potentially lethal infections with all of the resources available. Aother is to clean up the toxins, especially the endotoxins of gram negative bacteria and other debris which accumulate in the tissue and the blood as a result of the death of infectious microorganisms. The toxemia resulting from such accumulations is sometimes as dangerous, if not more so, to the health of the patient as the original infection. The presence of one or more compounds of this invention may help the body eliminate the endotoxins. The products of the invention may be coadministered with such materials as tetracycline, chlortetracycline, neomycin, erythromycin, novobiocin, penicillin, chloramphenicol and nitrofurazone.

The following non-limiting examples are given by way of illustration only.

In the examples, amino acid analysis was carried out on a Beckman-Spinco 119 Cl amino acid analyzer. Optical rotation was determined on a Perkin-Elmer Polarimeter Type 141.

EXAMPLE I

PREPARATION OF TUFTSINYL-TUFTSIN $N^G$-Tos-Arginyl-resin (I). Chloromethylated copolystyrene—1% divinyl benzene, 10 g (15 mmol Cl), was refluxed with 6.44 g (15 mmol) $N^\alpha$-Boc-$N^G$-Tos-arginine and 1.9 ml (13.5 mmol) triethylamine in 40 ml of absolute alcohol, at 80° C. for 48 h. The resin was then washed successively with ethanol, water, methanol, and methylene chloride and dried in vacuo. The yield of esterified Boc-tosyl-arginine was 0.260 mmol/g resin. The resulting Boc-Tos-arginyl-resin 2 g was deprotected at $N^\alpha$ by treatment with 50% trifluoroacetic acid in methylene chloride. After 30 min, the mixture was filtered and the resin washed three times each for 10 min with 20 ml of methylene chloride, followed by three washings with chloroform. It was then neutralized with 1 ml triethylamine in 19 ml chloroform and washed three times each for 10 min with 20 ml of chloroform and methylene chloride.

L-Prolyl-Tosyl-L-Arginyl-resin (II). Tos-arginyl-resin (I) containing 0.52 mmol of Tos-arginine was reacted with 0.33 g (1.56 mmol) Boc-L-proline and 0.32 g (1.56 mmol) of DCC in 15 ml methylene chloride. The reaction was continued for 2 h. The mixture was filtered and the dipeptide-resin was washed three times each for 10 min with 20 ml of absolute alcohol and then with methylene chloride followed by deprotection as above.

$N^\epsilon$-Z-L-Lysyl-L-Prolyl-Tos-L-Arginyl-resin (III). The deprotected dipeptide-resin (II) was allowed to react with 0.56 g (1.59 mmol) Boc-Z-L-lysine in the presence of 0.32 g (1.56 mmol) DCC in methylene chloride. The reaction and deprotection was carried out as described for (II).

O-Bzl-L-Threonyl-$N^\epsilon$-Z-L-lysyl-L-Prolyl-Tos-L-rginyl-resin (IV). The deprotected tripeptide-resin (III) was coupled with 0.48 g (1.56 mmol) of Boc-O-Bzl-threonine in the presence of 0.32 g (1.56 mmol) of DCC in methylene chloride. All subsequent reactions were carried out as for (III).

$N^G$-L-Arginyl-O-Bzl-L-Threonyl-$N^\epsilon$-Z-L-Lysyl-L-Proylyl-$N^G$-Tos-L-Arginine-resin (V). The product IV was coupled with 3.21 g (7.5 mmol) of BOC-$N^G$-Tos-L-rginine (DMF-$CH_2Cl_2$ 1:10 with 1.54 g (7.5 mmol) DCC, as above.

L-Proyl-$N^G$-Tos-L-Arginyl-O-Bzl-L-Threonyl-$N^\epsilon$-Z-L-Lysyl-L-Prolyl-$N^G$-Tos-L-Arginine-resin (VI). The product V was reacted with 0.58 (7.5 mmol) of BOC-L-proline and 1.54 g (5.7 mmol) of DCC as above.

$N^\epsilon$-Z-L-Lysyl-Pro-$N^G$-Tos-L-Arginyl-O-Bzl-L-Threonyl-$N^\epsilon$-Z-L-Lysyl-Pro-$N^G$-Tos-L-Arginine-resin (VII). The product VI was coupled with 2.85 g (7.5 mmol) of BOC-$N^\epsilon$-Z-L-lysine and with 1.54 g (7.5 mmol) DCC, as above.

O-Bzl-L-Threonyl-$N^\epsilon$-Z-L-Lysyl-L-Prolyl-$N^G$-Tos-L-Arginyl-O-Bzl-L-Threonyl-$N^\epsilon$-Z-L-Lysyl-L-Prolyl-$N^G$-L-Arginine-resin (VIII). The product was reacted with 2.38 g (7.5 mmol) of BOC-O-Bzl-L-threonine and 1.54 g (7.5 mmol), DCC. After reaction, the mixture was washed as above and deprotected with TFA as above. After deprotection, it was washed with dichloromethane and dried in vacuo at 40° C. to provide 9.4 g of the octapeptide resin.

Tuftsinyl-tuftsin (L-Threonyl-L-Lysyl-L-Prolyl-L-Arginyl-L-Threonyl-L-Lysyl-L-Prolyl-L-Arginine (IX). The octapeptide-resin (VIII) 9.4 g, was deprotected with TFMS-(8 ml) in anisole (4 ml), for 2 h at 40° C. After reaction, it was filtered, washed with anisole (5 ml) and triturated with dry ethyl ether. The white powder, was washed several times with ethyl ether. The residue was dissolved in 1% acetic acid and lyophilized to produce 1.85 g (61.6%) of fine powder. It was purified on a column of Sephadex C-25 (cationic-volume of column 31 ml) in two buffers: starting buffer 1.2 M pyridine-acetic acid pH 4.0 and limiting buffer 2.5 M pyridine-acetic acid pH 6.0 (60–114 ml fractions). After purification, 0.42 g fine powder was obtained. Amino acid analysis, $Thr_{0.99}LYS_{0.96}Pro_{0.95}Arg_{1.09}$; paper chromatography on Whatmann 3 paper in butanol:pyridine:acetic acid:water (30:20:6:24) $R_f = 0.04$; $[\alpha]_D^{25} = -24.5°$ (c 0.22, water); paper electrophoresis in 2% HCOOH, 700 V, 50 min—one spot.

EXAMPLE II

The following compounds are similarly prepared utilizing the appropriate optical isomers.

D-Threonyl-L-Lysyl-L-Prolyl-D-Arginyl-D-Threonyl-L-Lysyl-L-Prolyl-D-Arginine.

D-Threonyl-L-Lysyl-L-Prolyl-L-Arginyl-L-Threonyl-L-Lysyl-L-Prolyl-D-Arginine.

EXAMPLE III

PREPARATION OF TABLETS 1000 g of any one of the products of the previous examples and 2000 g of lactose were thoroughly mixed together and the whole was passed through a 30 mesh sieve.

A paste was separately prepared with 80 g of cornstarch and 350 ml of distilled water.

The mixture was well kneaded with the paste, the mass was passed through a 4 mesh sieve and the resulting globules were dried at 50° C. for 15 hours.

The dried globules were then granulated on a granulating machine and then passed through a 16 mest sieve. The grains were covered with a powdery mixture which had been prepared by blending 30 g of calcium stearate, 200 g of cornstarch and 80 g of talc, and then passed through a 40 mesh sieve.

Tablets each containing 250 mg of the selected product were made of the above-obtained granules in accordance with the conventional procedure known in the art.

EXAMPLE IV

PREPARATION OF INJECTION 100 g of the sodium salt of any one of the products prepared as described above were dissolved in distilled, pyrogen free water and made up to 5 liters. The solution was made isotonic with addition of a predetermined amount of an aqueous solution of physiological salt and filtered through a millipore bacterial filter.

EXAMPLE V

PREPARATION OF AN AQUEOUS SOLUTION FOR ORAL ADMINISTRATION

A mixture consisting of:
Cane sugar—g—100.0
Glycerine—ml—100.0
Ethyl p-oxybenzoate—g—1.5
Artificial organe essence—ml—0.2
Essential oil of orange—ml—1.0
together with 20.0 g of the hydrochloride salt of any one of the products prepared as described above was added to distilled, pyrogen free water to make up 1000 ml of the final volume.

What is claimed is:

1. Therapeutically useful non-antigenic polypeptides selected from the group consisting of:
   L-Thr-L-Lys-L-Pro-L-Arg-L-Thr-L-Lys-L-Pro-L-Arg,
   D-Thr-L-Lys-L-Pro-D-Arg-D-Thr-L-Lys-L-Pro-D-Arg,
   D-Thr-L-Lys-L-Pro-L-Arg-L-Thr-L-Lys-L-Pro-D-Arg
   and pharmacologically acceptable salts and derivatives thereof.

2. L-Thr-L-Lys-L-Pro-L-Arg-L-Thr-L-Lys-L-Pro-L-Arg and pharmacologically acceptable salts and derivatives thereof.

3. D-Thr-L-Lys-L-Pro-D-Arg-D-Thr-L-Lys-L-Pro-D-Arg and pharmacologically acceptable salts and derivatives thereof.

4. D-Thr-L-Lys-L-Pro-L-Arg-L-Thr-L-Lys-L-Pro-D-Arg and pharmacologically acceptable salts and derivatives thereof.

5. Pharmaceutical compositions containing a phagocytotically or pinocytotically stimulating or inhibiting amount of at least on compound selected from the group consisting of L-Thr-L-Lys-L-Pro-L-Arg-L-Thr-L-Lys-L-Pro-L-Arg, D-Thr-L-Lys-L-Pro-D-Arg-D-Thr-L-Lys-L-Pro-D-Arg, D-Thr-L-Lys-L-Pro-L-Arg-L-Thr-L-Lys-L-Pro-D-Arg, and pharmacologically acceptable salts and derivatives thereof together with a pharmaceutically acceptable excipient.

6. A composition as in claim 5 containing L-Thr-L-Lys-L-Pro-L-arg-L-Thr-L-Lys-L-Pro-L-Arg or a pharmacologically acceptable salt or derivative thereof.

7. A composition as in claim 5 containing D-Thr-L-Lys-L-Pro-D-Arg-D-Thr-L-Lys-L-Pro-D-Arg or a pharmacologically acceptable salt or derivative thereof.

8. A composition as in claim 5 containing D-Thr-L-Lys-L-Pro-L-Arg-L-Thr-L-Lys-L-Pro-D-Arg or a pharmacologically acceptable salt or derivative thereof.

9. A method of stimulating or inhibiting phagocytosis or pinocytosis in a mammalian patient in need of such stimulation or inhibition which comprises administering to such patient a stimulating or inhibiting amount of at least one compound selected from the group consisting of:
   L-Thr-L-Lys-L-Pro-L-Arg-L-Thr-L-Lys-L-Pro-L-Arg,
   D-Thr-L-Lys-L-Pro-D-Arg-D-Thr-L-Lys-L-Pro-D-Arg,
   D-Thr-L-Lys-L-Pro-L-Arg-L-Thr-L-Lys-L-Pro-D-Arg
   and pharmaceutically acceptable salts and derivatives thereof.

10. A method as in claim 9 wherein the compound is L-Thr-L-Lys-L-Pro-L-Arg-L-Thr-L-Lys-L-Pro-L-Arg or a pharmacologically acceptable salt or derivative thereof.

11. A method as in claim 9 wherein the compound is D-Thr-L-Lys-L-Pro-D-Arg-D-Thr-L-Lys-L-Pro-D-Arg or a pharmacologically acceptable salt or derivative thereof.

12. A method as in claim 9 wherein the compound is D-Thr-L-Lys-L-Pro-L-Arg-L-Thr-L-Lys-L-Pro-D-Arg or a pharmacologically acceptable salt or derivative thereof.

UNITED STATES PATENT AND TRADEMARK OFFICE
CERTIFICATE OF CORRECTION

PATENT NO. : 4,390,528
DATED : June 28, 1983
INVENTOR(S) : Victor A. Najjar

It is certified that error appears in the above-identified patent and that said Letters Patent are hereby corrected as shown below:

Col. 3, line 29, Insert the word --coated-- after the word "enteric"

Col. 8, line 28, "pharmaceutically" should read --pharmacologically--

Signed and Sealed this

Twenty-first Day of February 1984

[SEAL]

Attest:

Attesting Officer

GERALD J. MOSSINGHOFF

Commissioner of Patents and Trademarks